US011103222B2

(12) United States Patent
Bharat et al.

(10) Patent No.: US 11,103,222 B2
(45) Date of Patent: Aug. 31, 2021

(54) SYSTEM AND METHOD FOR FAST AND AUTOMATED ULTRASOUND PROBE CALIBRATION

(71) Applicant: KONINKLIJKE PHILIPS N.V., Eindhoven (NL)

(72) Inventors: Shyam Bharat, Arlington, MA (US); Antonio Bonillas Vaca, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 154 days.

(21) Appl. No.: 16/471,796

(22) PCT Filed: Dec. 18, 2017

(86) PCT No.: PCT/IB2017/058037
§ 371 (c)(1),
(2) Date: Jun. 20, 2019

(87) PCT Pub. No.: WO2018/116114
PCT Pub. Date: Jun. 28, 2018

(65) Prior Publication Data
US 2020/0085413 A1    Mar. 19, 2020

Related U.S. Application Data

(60) Provisional application No. 62/437,284, filed on Dec. 21, 2016.

(51) Int. Cl.
*A61B 8/00* (2006.01)
*A61B 8/08* (2006.01)

(52) U.S. Cl.
CPC ............ *A61B 8/587* (2013.01); *A61B 8/0841* (2013.01); *A61B 8/4218* (2013.01);
(Continued)

(58) Field of Classification Search
CPC ........... A61B 8/00; A61B 8/08; A61B 8/0833; A61B 8/0841; A61B 8/42; A61B 8/4209;
(Continued)

(56) References Cited

U.S. PATENT DOCUMENTS

2015/0269728 A1*  9/2015  Parthasarathy ...... A61B 8/4245
                                                                382/131
2016/0038119 A1*  2/2016  Desjardins ......... A61B 17/3403
                                                                600/424
(Continued)

FOREIGN PATENT DOCUMENTS

WO    2014016736 A2    1/2014
WO    2018115143 A1    6/2018

OTHER PUBLICATIONS

Luan et al:"Automatic and Robust Freehand Ultrasound Calibration Using a Tracked Pointer"; Jounral of Japan Sockiety of Computer Aided Surgery, vol. 13, No. 4, Jan. 2011, pp. 437-443.
(Continued)

*Primary Examiner* — Hoai-An D. Nguyen

(57) ABSTRACT

An apparatus (10) for calibrating electromagnetic (EM) tracking of an associated ultrasound probe (12) includes a calibration needle (16), an EM tracking device including a field generator (14) and a reference EM sensor (24), an EM sensor (18, 26) on the ultrasound probe and on the calibration needle; at least one processor (50); and a non-transitory storage medium storing instructions to perform a EM tracking calibration method including: determining a location of the calibration needle in an ultrasound imaging space at a measurement time using the ultrasound probe; determining an EM-tracked location of the calibration needle at the measurement time; and generating a registration relating the location of the calibration needle in the ultrasound imaging space and the EM-tracked location of the calibration needle at the measurement time.

12 Claims, 9 Drawing Sheets

(52) U.S. Cl.
CPC .......... *A61B 8/4254* (2013.01); *A61B 8/4245* (2013.01); *A61B 8/58* (2013.01)

(58) Field of Classification Search
CPC ... A61B 8/4218; A61B 8/4245; A61B 8/4254; A61B 8/52; A61B 8/5215; A61B 8/5238; A61B 8/5261; A61B 8/58; A61B 8/587
USPC ..... 324/200, 202, 500, 537, 750.01, 750.02, 324/76.11, 130; 600/300, 407, 424
See application file for complete search history.

(56) References Cited

U.S. PATENT DOCUMENTS

| | | | |
|---|---|---|---|
| 2016/0258782 A1* | 9/2016 | Sadjadi | ................ G01D 18/008 |
| 2017/0014192 A1* | 1/2017 | Bharat | ................... A61B 5/062 |
| 2019/0159752 A1* | 5/2019 | Bharat | ................... A61B 34/20 |

OTHER PUBLICATIONS

PCT/EP2017/058037 Written Opinion and ISR, dated Jun. 7, 2018, 21 Pages.
Zhang et al: "Freehand 3D Ultrasound Calibration Using an Electromagnetically Tracked Needle";Proceedings of SPIE, Medical Imaging 2006: Visualization, Image-Guided Procedures and Display, vol. 6141, Mar. 2006, pp. 61412M-1.

\* cited by examiner

| EM tracking data |
|---|
| $X_1$ |
| $X_2$ |
| $X_3$ |
| $c_4 X_3 + d_4 X_4$ |
| $X_4$ |
| $X_5$ |
| $X_6$ |
| $c_8 X_6 + d_8 X_4$ |
| $X_7$ |
| $X_8$ |
| $X_9$ |
| $X_{10}$ |
| $X_{11}$ |
| $X_{12}$ |

| US tracking data |
|---|
| |
| |
| |
| $(X_1, Y_1)$ |
| $(a_4 X_1 + b_4 X_2, a_4 Y_1 + b_4 Y_2)$ |
| $(a_5 X_1 + b_5 X_2, a_5 Y_1 + b_5 Y_2)$ |
| $(X_2, Y_2)$ |
| $(a_7 X_2 + b_7 X_3, a_7 Y_2 + b_7 Y_3)$ |
| $(X_3, Y_3)$ |
| $(a_9 X_3 + b_9 X_4, a_9 Y_3 + b_9 Y_4)$ |
| $(a_{10} X_3 + b_{10} X_4, a_{10} Y_3 + b_{10} Y_4)$ |
| $(X_4, Y_4)$ |
| $(a_{12} X_4 + b_{12} X_5, a_{12} Y_4 + b_{12} Y_5)$ |
| $(a_{13} X_4 + b_{13} X_5, a_{13} Y_4 + b_{13} Y_5)$ |
| $(X_5, Y_5)$ |

| Time |
|---|
| $T_1$ |
| $T_2$ |
| $T_3$ |
| $T_4$ |
| $T_5$ |
| $T_6$ |
| $T_7$ |
| $T_8$ |
| $T_9$ |
| $T_{10}$ |
| $T_{11}$ |
| $T_{12}$ |
| $T_{13}$ |
| $T_{14}$ |

FIG. 10

| Time | US tracking data | EM tracking data |
|---|---|---|
| $T_1$ | | $X_1$ |
| $T_2$ | | $X_2$ |
| $T_3$ | $(X_1, Y_1)$ | $X_3$ |
| $T_4$ | $(X_1, Y_1)$ | $X_3$ |
| $T_5$ | $(X_1, Y_1)$ | $X_4$ |
| $T_6$ | $(X_2, Y_2)$ | $X_5$ |
| $T_7$ | $(X_2, Y_2)$ | $X_6$ |
| $T_8$ | $(X_3, Y_3)$ | $X_6$ |
| $T_9$ | $(X_3, Y_3)$ | $X_7$ |
| $T_{10}$ | $(X_3, Y_3)$ | $X_8$ |
| $T_{11}$ | $(X_4, Y_4)$ | $X_9$ |
| $T_{12}$ | $(X_4, Y_4)$ | $X_{10}$ |
| $T_{13}$ | $(X_4, Y_4)$ | $X_{11}$ |
| $T_{14}$ | $(X_5, Y_5)$ | $X_{12}$ |
| $T_{15}$ | $(X_5, Y_5)$ | $X_{13}$ |

FIG. 11

SYSTEM AND METHOD FOR FAST AND AUTOMATED ULTRASOUND PROBE CALIBRATION

CROSS-REFERENCE TO PRIOR APPLICATIONS

This application is the U.S. National Phase application under 35 U.S.C. § 371 of International Application No. PCT/IB2017/058037, filed on Dec. 18, 2017 which claims the benefit of U.S. Provisional Patent Application No. 62/437,284, filed on Dec. 21, 2016. These applications are hereby incorporated by reference herein.

FIELD

The following relates generally to the ultrasound arts, calibration arts, probe tracking arts, electromagnetic tracking arts, image guided medical procedure arts, and related arts.

BACKGROUND

In medical procedures involving a tracked ultrasound (US) probe (such as an electromagnetically (EM)-tracked US probe), the EM tracker on the probe has to be registered to the US imaging array, a process called "calibration". This calibration has to be highly accurate, to ensure the correct interpretation of US images during the procedure.

In a typical US probe calibration method, the user manually identifies (on an US image) the tip of an EM-tracked needle inserted in a tissue-mimicking or water phantom (e.g. using a mouse click), while the EM tracking system records the corresponding location of the EM sensor. The position and orientation of a static reference EM sensor are also recorded. Then, using the below equation, the registration between the US imaging array and the EM sensor on the US probe ($T_{US\_ProbeEM}$) is obtained.

$$T_{ProbeEM\_RefEM} \times T_{US\_ProbeEM} \times p_{US}(x,y,0) = T_{NeedleEM\_RefEM} \times p_{EM}(x,y,z) \quad (1)$$

Where pUS (x,y,0) is the needle tip clicked by the user on the 2D US image, $p_{EM}$ (x,y,z) is the 3D location of the needle EM sensor (calibrated to the needle tip) saved by the EM tracking system at the time of the user click, $T_{NeedleEM\_RefEM}$ is the known transformation from the needle EM sensor to the static reference sensor and $T_{ProbeEM\_RefEM}$ is the known transformation from the EM sensor on the US probe to the static reference sensor. The EM field generator (FG) can also serve as the reference coordinate system (instead of a specific reference sensor) to which all other tracked quantities are transformed.

Current US tracking technology estimates the position of a passive ultrasound sensor (e.g., PZT, PVDF, copolymer or other piezoelectric material) mounted on the tracked surgical tool in the field of view (FOV) of a conventional diagnostic US B-mode image by analyzing the signal received by the ultrasound sensor as the beams of the imaging probe sweep the FOV. Time-of-flight measurements provide the axial/radial distance of the passive ultrasound sensor from the imaging array, while amplitude measurements and knowledge of the beam firing sequence provide the lateral/angular position of the sensor. When used with 3D transducers (i.e., 2D matrix arrays), the elevational position of the sensor can also be obtained in a similar manner. Therefore, the 3D position of the sensor can be estimated in real-time, provided it is present within the FOV of the imaging transducer.

Current methods to perform the US probe calibration are usually manual, subjective and therefore, error-prone, apart from being time-consuming and tedious to perform. With respect to equation (1) above, any errors in the user identification of the needle tip (i.e., in $p_{US}$ (x,y,0)) will propagate to errors in the estimation of the probe calibration $T_{US\_ProbeEM}$.

The following proposes a fast and automated method to calibrate a tracked US probe, thus, removing the subjectivity associated with current methods, while ensuring high accuracy.

Interventional procedures often involve multi-modality imaging protocols for diagnosis and/or navigational guidance. For example, magnetic resonance imaging (MRI) can be used as a pre-procedural imaging modality primarily for diagnosis, segmentation etc. and ultrasound (US) for intra-procedural guidance. In such cases, the intra-procedural US (which is most often two dimensional (2D)) has to be registered to the pre-procedural MRI. To spatially interpret ultrasound images correctly in such interventional procedures, a tracking system, typically an electromagnetic (EM) tracking system, is employed. In EM tracking, a field generator produces a low intensity electromagnetic field that varies spatially so as to produce EM-encoded space. A stationary reference EM sensor is placed in this field, and a probe EM sensor is attached to the ultrasound probe. A small electrical current is induced in each sensor by the spatially encoded EM field, and is used to determine position in the EM field, referenced to the position of the EM reference sensor or to the EM field generator (FG). Such EM tracking systems are commercially available, for example the Aurora EM tracking system from Northern Digital Inc. (NDI), Ontario, Canada.

For correct spatial interpretation of the ultrasound images, it is further necessary to spatially register the ultrasound image to the position of the EM sensor on the ultrasound probe. This is defined as a transformation $T_{US\_ProbeEM}$ where ProbeEM denotes the position of the EM sensor on the US probe. Currently, this is done as a manual procedure. A calibration needle including an EM sensor at or close to the needle tip (and calibrated to the needle tip, so that the reported EM position is that of the needle tip) is imaged by ultrasound while being tracked by the EM tracking. In the ultrasound image, the user manually marks the location of the needle tip. The EM position of the needle EM sensor is recorded at the time of the manual user click, and the relation:

$$T_{ProbeEM\_RefEM} \times T_{US\_ProbeEM} \times p_{US}(x,y,0) = T_{NeedleEM\_RefEM} \times p_{EM}(x,y,z) \quad (1)$$

is solved for US image position→probe EM sensor position transformation $T_{US\_ProbeEM}$. Then the transformation $T_{US\_RefEM} = T_{ProbeEM\_RefEM} \times T_{US\_ProbeEM}$ locates the ultrasound image with reference to the reference EM sensor (where $T_{ProbeEM\_RefEM}$ is the known transformation from the EM sensor on the US probe to the static reference EM sensor).

This approach has some disadvantages. It is labor-intensive, particularly because the just-described process is preferably repeated for a dozen or more different locations to map out the space. Additionally, errors can be introduced if the needle tip is not located precisely by the operator/user in the two-dimensional (2D) plane of the ultrasound image sweep.

Improvements disclosed herein address the foregoing and other disadvantages of existing tracking systems, methods, and the like.

BRIEF SUMMARY

In accordance with one illustrative example, an apparatus for calibrating electromagnetic (EM) tracking of an associated ultrasound probe includes an EM tracking device including a field generator configured to generate an EM field in an EM-encoded space and a reference EM sensor, an EM sensor disposed on the ultrasound probe, a calibration needle; an EM sensor disposed on the calibration needle; at least one processor; and a non-transitory storage medium storing instructions readable and executable by the at least one processor to perform a EM tracking calibration method including: determining a location of the calibration needle in an ultrasound imaging space at a measurement time using the ultrasound probe; determining an EM-tracked location of the calibration needle at the measurement time from EM tracking by the EM tracking device of the EM sensor disposed on the calibration needle; and generating a registration relating the location of the calibration needle in the ultrasound imaging space at the measurement time and the EM-tracked location of the calibration needle at the measurement time.

In accordance with another illustrative example, an apparatus for calibrating tracking of an associated ultrasound probe includes: a tracking device configured to locate tracking sensors in a tracking space; an ultrasound probe tracking sensor disposed on the ultrasound probe; a calibration needle; a calibration needle tracking sensor disposed on a calibration needle; at least one processor; and a non-transitory storage medium storing instructions readable and executable by the at least one processor to perform a tracking calibration method including: determining a location of the calibration needle in an ultrasound imaging space at a measurement time using the ultrasound probe; determining a tracked location of the calibration needle at the measurement time from tracking by the tracking device of the calibration needle tracking sensor disposed on the calibration needle; and generating a registration relating the location of the calibration needle in the ultrasound imaging space at the measurement time and the tracked location of the calibration needle at the measurement time.

In accordance with another illustrative example, an apparatus for calibrating tracking of an associated ultrasound probe includes: a tracking device configured to locate tracking sensors in a tracking space; an ultrasound probe tracking sensor disposed on the ultrasound probe; a calibration needle; a calibration needle tracking sensor disposed on a calibration needle; an ultrasound transducer disposed on the calibration needle; at least one processor; and a non-transitory storage medium storing instructions readable and executable by the at least one processor to perform a EM tracking calibration method including: performing an ultrasound sweep comprising a plurality of ultrasound beams emitted in different directions by the ultrasound probe; detecting a transducer signal generated by the ultrasound transducer in response to sonication of the ultrasound transducer during the ultrasound sweep; determining a measurement time as a time stamp of the detected transducer signal; determining a location of the calibration needle in an ultrasound imaging space at the measurement time from a direction of the ultrasound beam that sonicated the ultrasound transducer and comparison of the measurement time with a trigger time of the ultrasound beam that sonicated the ultrasound transducer and the time-of-flight along the ultrasound beam; determining a tracked location of the calibration needle at the measurement time from tracking by the tracking device of the calibration needle tracking sensor disposed on the calibration needle; and generating a registration relating the location of the calibration needle in the ultrasound imaging space at the measurement time and the tracked location of the calibration needle at the measurement time.

One advantage resides in providing faster and automated ultrasound probe calibration.

Another advantage resides in in reducing errors in ultrasound probe calibration.

Further advantages of the present disclosure will be appreciated to those of ordinary skill in the art upon reading and understand the following detailed description. It will be appreciated that a given embodiment may provide none, one, two, or more of these advantages.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the invention.

FIGS. 10 and 11 show interpolation approaches for performing a synchronization operation of FIG. 3.

DETAILED DESCRIPTION

Some embodiments disclosed herein replace the manual labeling of the needle tip in an ultrasound image with an automated process. In one embodiment, the calibration needle tip is modified by adding an additional ultrasound transducer, which emits a signal in response to being sonicated during the ultrasound sweep. This transducer signal is time stamped, recorded, and synchronized with the time-stamped EM data. The ultrasound sweep includes outputting a trigger signal marking the start of each ultrasound beam emission, and so location of the transducer in the 2D ultrasound sweep plane is determined based on which beam sonicated the transducer along with the "time of flight" of the beam to the transducer (effectively one-half of the echo time of US imaging since the return echo is not used). This automatically determined location in US image space is substituted for the manually labeled position in the ultrasound image.

In alternative embodiments, other options can be used instead of the needle-placed ultrasound transducer. In one approach, the transducer is replaced by a passive ultrasound reflector and the echo is detected using the ultrasound probe in receive mode. For example, the ultrasound sensor disposed on a calibration needle "listens" to the emitted ultrasound beams from the ultrasound probe and re-emits an acoustic pulse that can be detected by the ultrasound probe. In another approach, the needle tip is designed to be visible in an ultrasound image, and image processing is used to detect the needle location in the ultrasound image.

To address the problem that the needle tip may not be precisely in the 2D ultrasound sweep plane, either the needle tip can be moved linearly approximately transverse to the 2D plane, or the ultrasound probe can be rocked or moved linearly to sweep the 2D plane across a stationary needle tip. The ultrasound sweep for which the signal from the needle tip (transducer signal in the main embodiment, or ultrasound echo strength or image contrast in the alternative embodiments) is largest is then used for the calibration. The requisite motion of the needle tip or ultrasound probe can be provided by a robotic apparatus, or can be done manually since the timestamped data are stored and the sweep providing the strongest signal can then be identified retrospectively.

Figure 1:
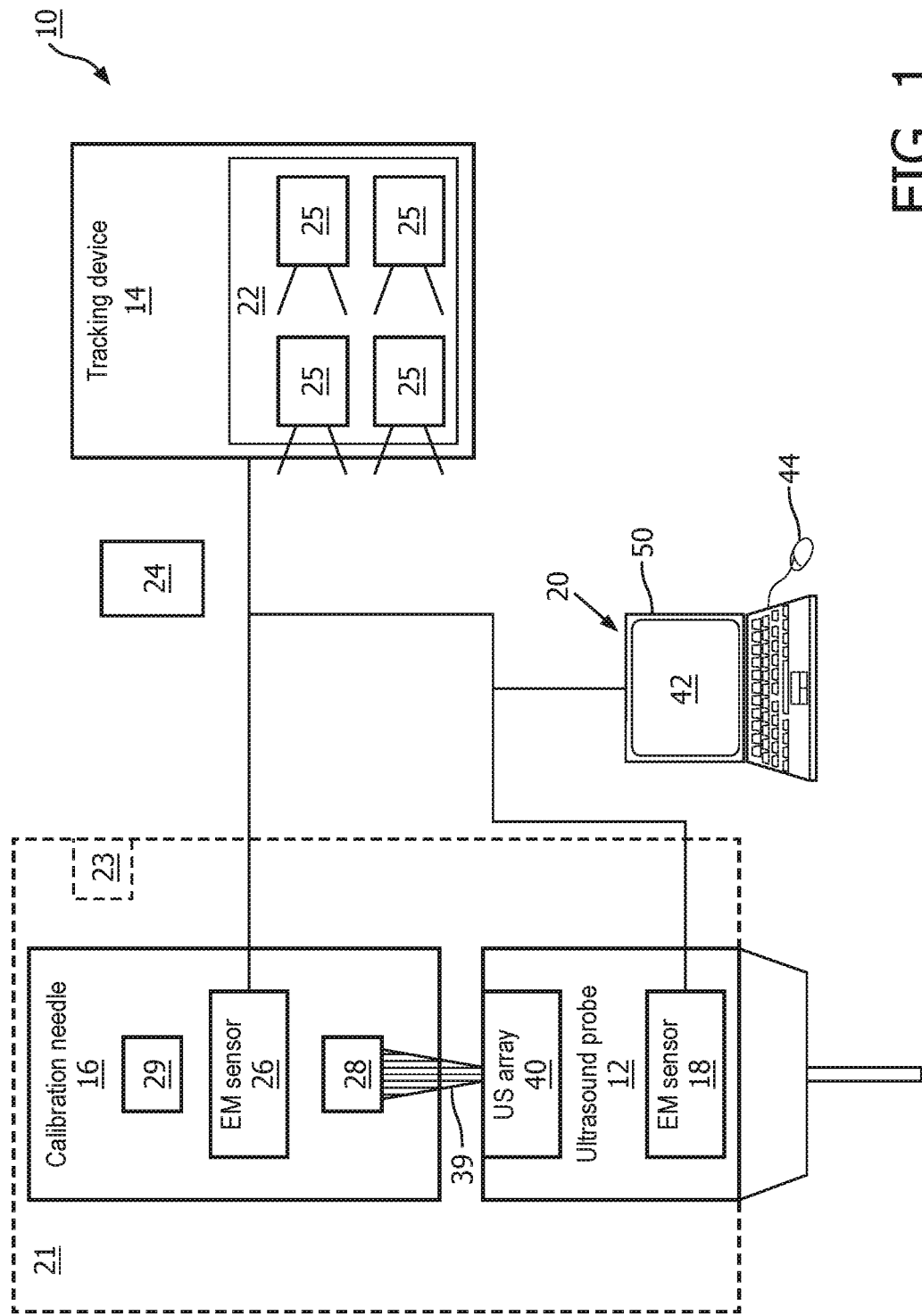
FIG. 1 diagrammatically illustrates an apparatus for calibrating a tracking process of an ultrasound probe according to one aspect.

With reference now to FIG. 1, a schematic illustration of an apparatus 10 for calibrating electromagnetic (EM) tracking of an associated ultrasound probe 12 is shown. The apparatus 10 includes an EM tracking device 14, a calibration needle 16, an EM sensor 18 that is disposed on the ultrasound probe 12; and at least one computer 20 (and optionally, a robotic apparatus 21 configured to move the calibration needle 16 relative to the ultrasound probe 12), each of these components being described in more detail below.

The EM tracking device 14 is configured to locate one or more tracking sensors in a tracking space. In one example, the EM tracking device 14 includes a field generator 22 configured to generate an EM field in an EM-encoded tracking space containing both the ultrasound probe 12 and the calibration needle 16. The EM tracking device 14 also optionally includes a reference EM sensor 24 located in the EM-encoded space. The EM tracking device 14 is configured to locate tracking EM sensors (e.g., a calibration needle EM sensor 26 located on the calibration needle 16 and/or the probe EM sensor 18 located on the ultrasound probe 12) in the EM-encoded tracking space relative to the reference EM sensor 24 or relative to the field generator 22. The EM tracking device 14 can be any commercially-available EM tracking device, such as the Aurora Electromagnetic Tracking System (available from Northern Digital, Inc., Waterloo, Ontario, Canada), or can be a custom-built device.

The calibration needle EM sensor 26 is configured to detect the generated EM field by the EM tracking device 14. At least one ultrasound transducer 28 is also disposed on the calibration needle 16 and is configured to detect sonication of the needle tip by the ultrasound probe 12. While EM tracking is described herein, any other tracking system can be employed that is capable of tracking position of the calibration needle. For example, the calibration needle 16 may alternatively include reflective echogenic tracking sensors 29 which are tracked by an optical tracking device (not shown).

Figure 2:
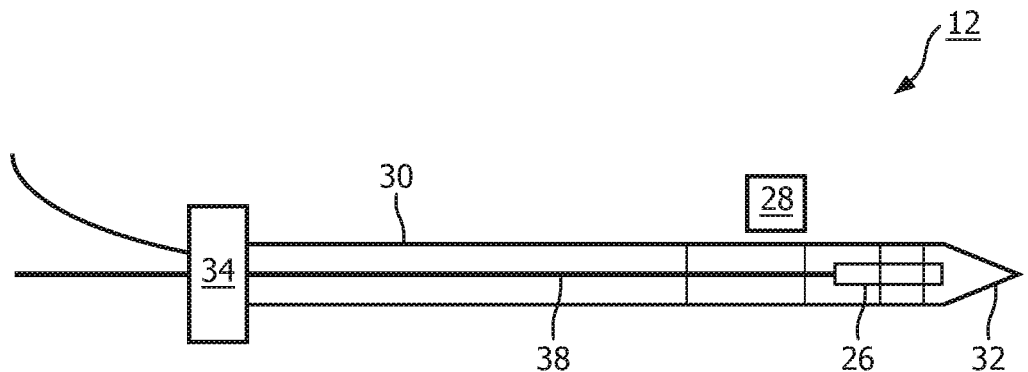
FIG. 2 diagrammatically illustrates the calibration needle of the apparatus of FIG. 1.

Referring now to one embodiment shown in FIG. 2, the calibration needle 16 may include a needle body 30 with a needle tip 32 disposed at a first end of the needle body and a wiring hub 34 disposed at a second opposing end of the needle body. The EM sensor 18 (not shown in FIG. 2) may be disposed at the needle tip 32 or at a known distance from the needle tip 32 within an interior of the needle body 30 or integrated into the walls of the needle body. The EM sensor 18 is configured to detect the generated EM field by the EM tracking device 14. The ultrasound transducer 28 is also located at or at a known distance from the needle tip 32. The relative positions of EM sensor 18 and the ultrasound transducer 28 are assumed to be known a priori, e.g. spatially registered using orthogonal x-ray or fluoroscopy or CT imaging of the needle (alternately, both the EM and US sensor positions are registered to the needle tip). Wiring 38, preferably in the interior of the probe body 30, connects to the EM sensor 18 and the ultrasound sensor 28, e.g. using the hub 34 as a wiring feedthrough.

Referring back to FIG. 1, the at least one computer 20 includes typical components, such as at least one display component 42, at least one user input component 44, at least one electronic processor 50 (e.g. a microprocessor, multi-core microprocessor, or so forth) programmed to perform calibration functions as disclosed herein. In some examples, the display 42 can be a touch-sensitive display. The user input component 44 can be a mouse, a keyboard, a stylus, an aforementioned touch-sensitive display, a microphone, and/or the like.

Figure 3:
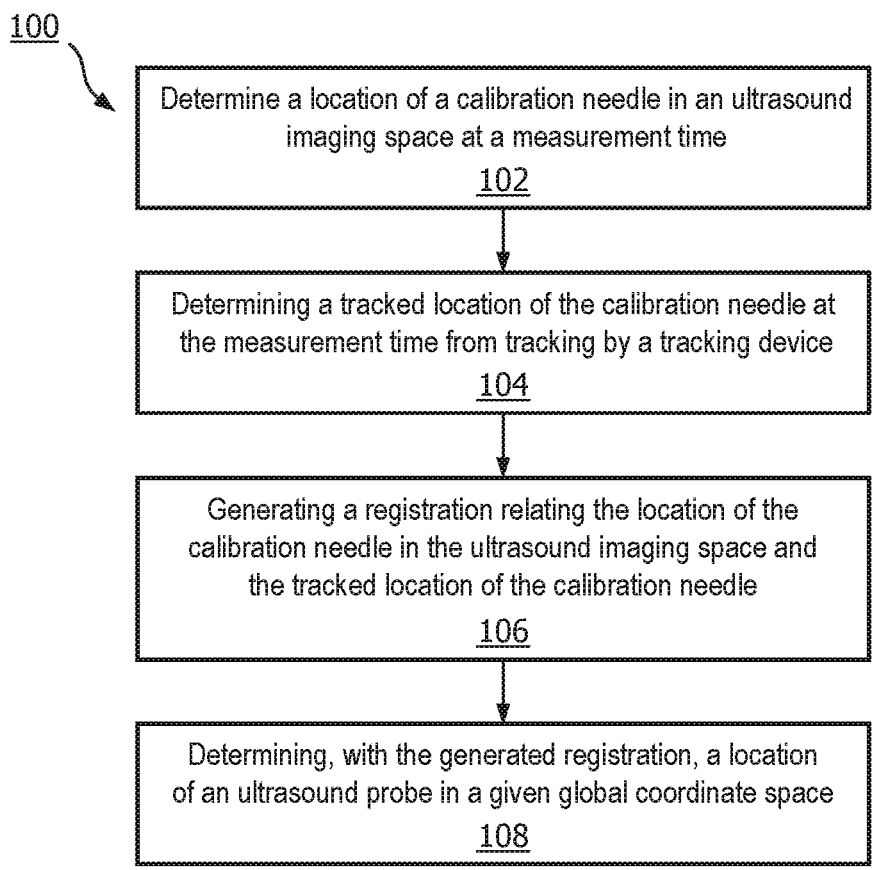
FIG. 3 is an exemplary flow chart of the calibration process of the apparatus of FIG. 1.

With reference now to FIG. 3, the at least one processor 50 is programmed to perform an EM tracking calibration method 100 of the ultrasound probe 12 in the EM encoded space. At step 102, a location of the calibration needle 16 in an ultrasound imaging space is determined at a measurement time using the ultrasound probe 12 and the ultrasound transducer 28. This is the value $p_{US}(x,y,0)$ in Equation (1). At step 104, a tracked location (e.g., an EM-tracked location) of the calibration needle 16 is determined at the measurement time from tracking (e.g., EM tracking) by the tracking device 14 of the EM sensor 26 disposed on the calibration needle 16. This is the position $p_{EM}(x,y,z)$ in Equation (1). At the same time, the EM tracking system is monitoring the position of the reference EM sensor 24. From this, the transform $T_{NeedleEM\_RefEM}$ is determined. At a step 106, a tracked location (e.g., an EM-tracked location) of the ultrasound probe 12 is determined at the measurement time from tracking (e.g., EM tracking) by the tracking device 14 of the EM sensor 18 disposed on the ultrasound probe 12. From this along with the tracked position of the reference EM probe 24 the transform $T_{ProbeEM\_RefEM}$ is determined. Thus, at step 108, a registration ($T_{US\_ProbeEM}$) relating the location $p_{US}(x,y,0)$ of the calibration needle 16 in the ultrasound imaging space at the measurement time and the tracked location $p_{EM}(x,y,z)$ of the calibration needle at the measurement time is generated by solving Equation (1) for $T_{US\_ProbeEM}$.

Figure 4:
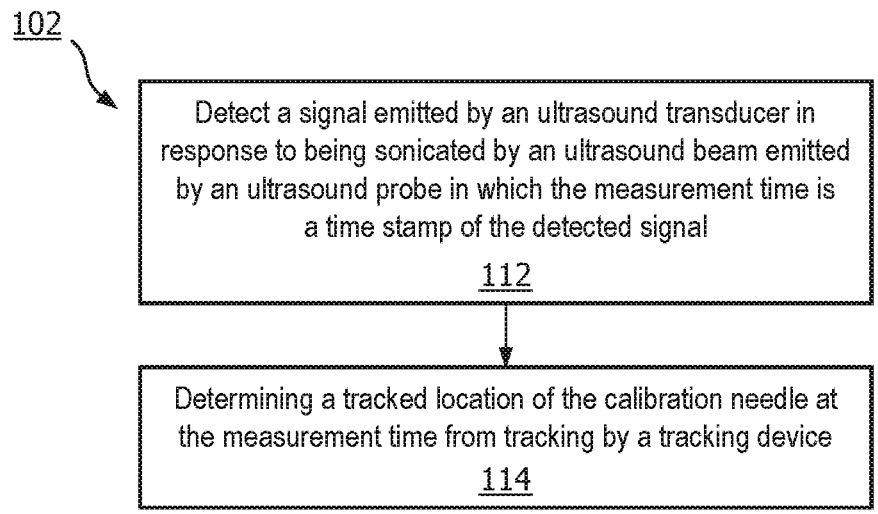
FIGS. 4-7 are exemplary flow charts of alternative operations of the calibration process of FIG. 3.

As shown in FIGS. 4-9, the step 102 of determining the location $p_{US}(x,y,0)$ of the calibration needle 16 in the ultrasound imaging space at the measurement time using the ultrasound probe 12 can be performed in a variety of methods. In one embodiment, as shown in FIG. 4, step 102 includes: detecting a signal emitted by the ultrasound transducer 28 in response to being sonicated by an ultrasound beam 39 emitted by an ultrasound transducer array 40 of the ultrasound probe 12 (see FIG. 1), in which the measurement time is a time stamp of the detected signal (112); and determining the location of the calibration needle 16 in the ultrasound imaging space from a direction of the ultrasound beam 39 and comparison of the measurement time with a trigger time of the ultrasound beam (114). This comparison yields the "time of flight" of the ultrasound beam from the array 40 to the transducer 28.

Figure 5:
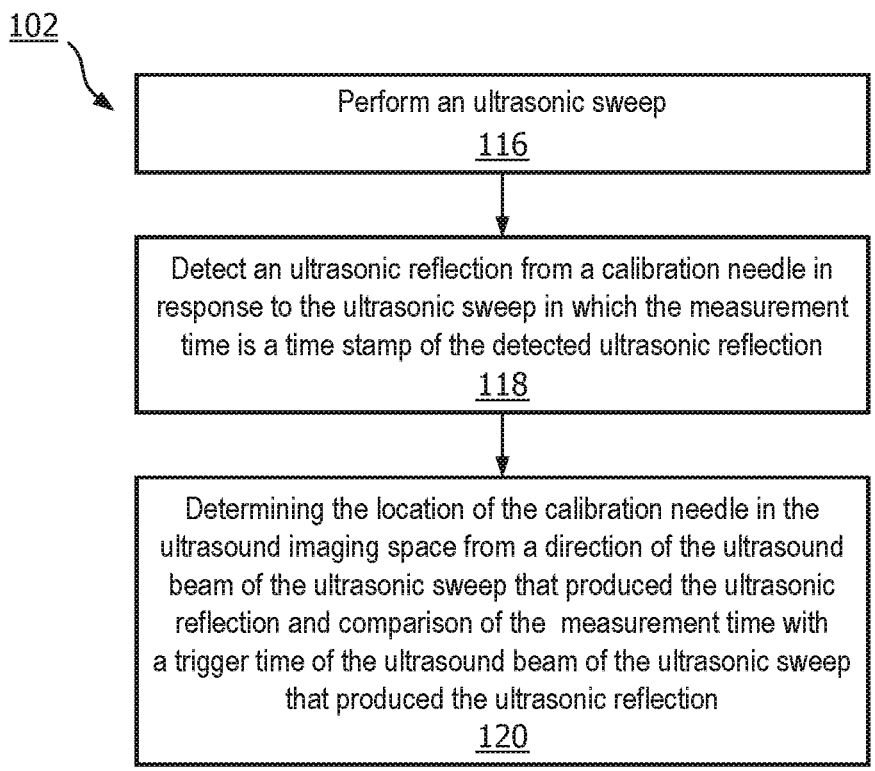

In another embodiment, as shown in FIG. 5, step 102 includes: performing an ultrasonic sweep using the ultrasound probe 12 (116); detecting, with the ultrasound probe 12, an ultrasonic transmission from the calibration needle 16 in response to the ultrasonic sweep in which the measurement time is a time stamp of the detected ultrasonic reflection (118); and determining the location of the calibration needle 16 in the ultrasound imaging space from a direction of the ultrasound beam of the ultrasonic sweep that produced the ultrasonic transmission from the sensor and comparison of the measurement time with a trigger time of the ultrasound beam of the ultrasonic sweep that produced the ultrasonic transmission from the sensor (120). This comparison yields the "echo time" of the ultrasound beam from the array 40 to the calibration needle 16 and back to the ultrasound transducer array 40, and hence is twice the "time-of-flight" of the previous embodiment.

Figure 6:
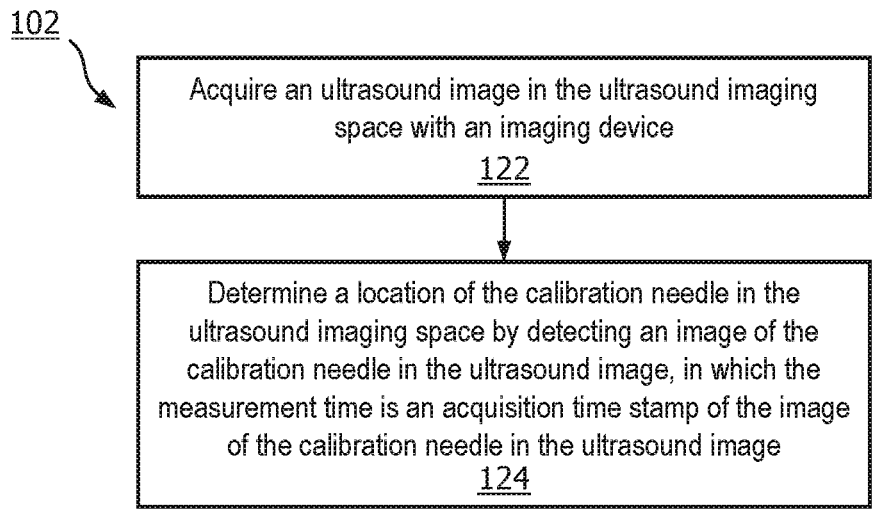

In a further embodiment, as shown in FIG. 6, step 102 includes: acquiring an ultrasound image in the ultrasound imaging space with an imaging device (e.g., with an ultrasound imaging device, which is not shown) (122); and determining the location of the calibration needle 16 in the ultrasound imaging space by detecting an image of the calibration needle in the ultrasound image, in which the measurement time is an acquisition time stamp of the image of the calibration needle in the ultrasound image (124). In one example, the acquisition time stamp of the image can be the time of image acquisition, under the assumption that the acquisition time for the entire image is small. In another example, the acquisition time stamp of the image can be the exact time of sonication of the calibration needle (similar to the time stamp determined at 112), thus providing a more precise time value. Determination of the location of the calibration needle 16 in the ultrasound image can use any suitable image segmentation or feature recognition technique, such as matched filtering using a known filter kernel representing the calibration needle in the image. In this example, the reflective sensors 29 comprise an echogenic strip or beacon at the tip of the calibration needle 16.

In the foregoing, it is assumed that the EM tracking measurements and the ultrasound data are both time stamped to enable synchronization between the two sets of measurements. This synchronization can be complicated if the sampling time intervals for EM and ultrasound are not synchronized. This can be addressed by suitable interpolation techniques.

The foregoing disclosed calibration techniques assume the calibration needle 16 is located in the ultrasound beam generated by the ultrasound transducer array 40 of the ultrasound probe 12. This assumption is likely to be correct if the ultrasound transducer array 40 is a three-dimensional (3D) array, but less likely if it is a two-dimensional (2D) array. In the latter case, an automated approach for relatively moving the ultrasound probe 12 and calibration needle 16 can be used to determine when the calibration needle 16 is optimally positioned in the 2D ultrasound plane.

Figure 7:
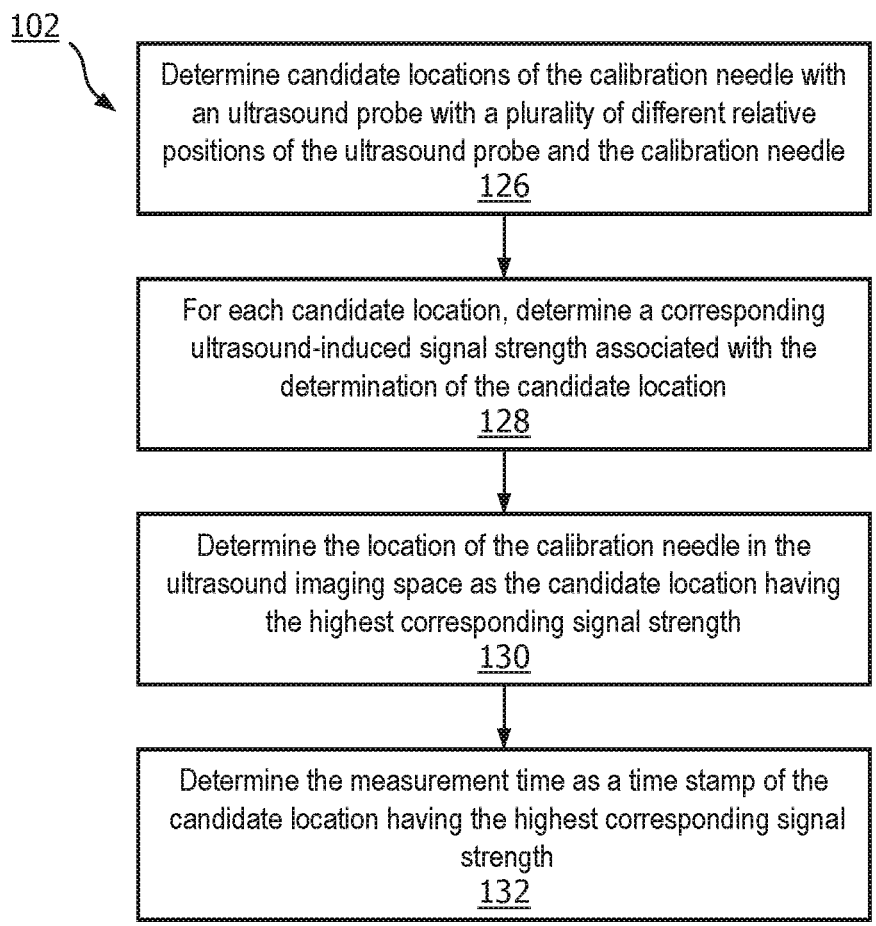
Figure 8:
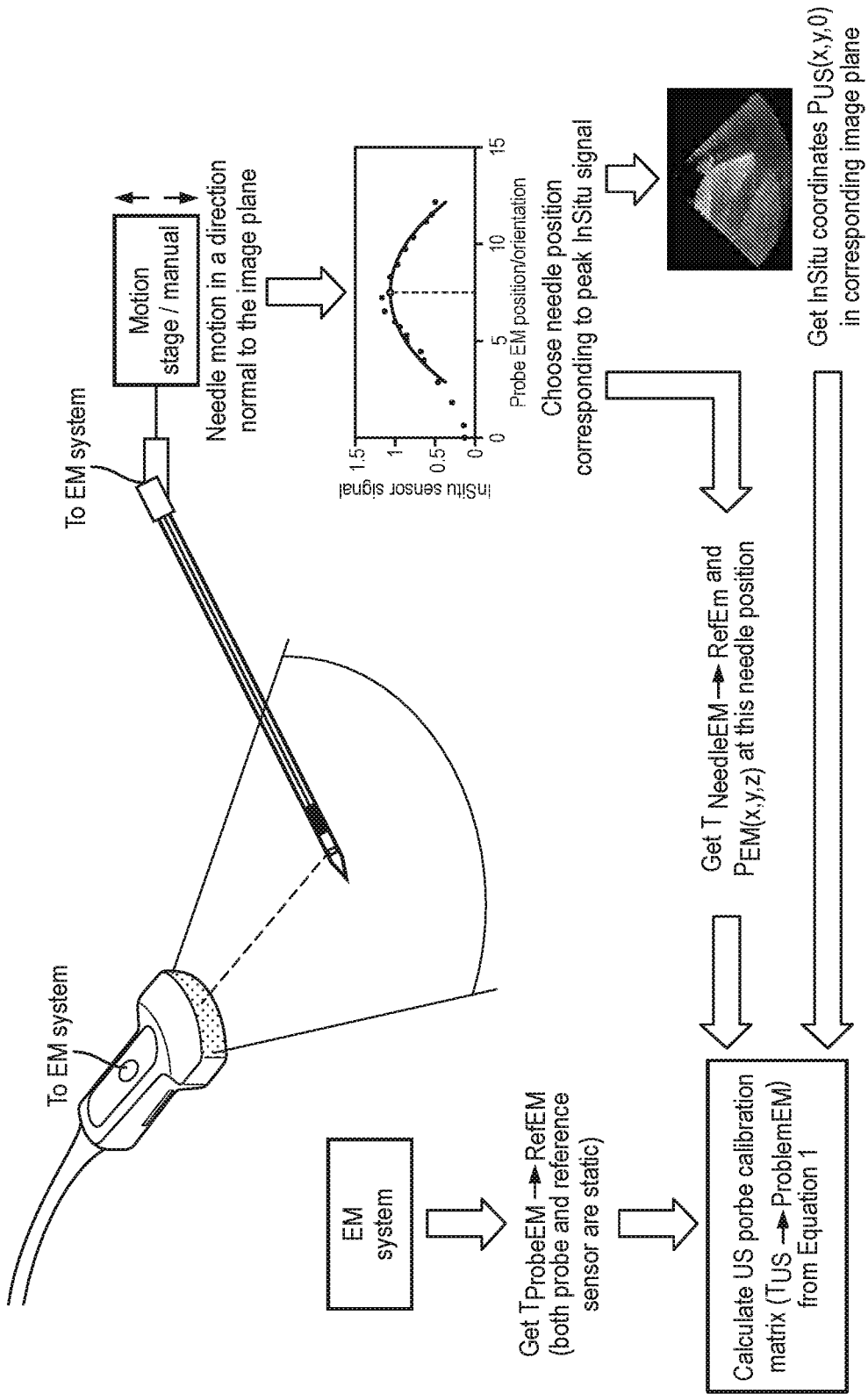
FIG. 8 diagrammatically illustrates a calibration process of the apparatus of FIG. 1 in which the needle is moved relative to the probe.
Figure 9:
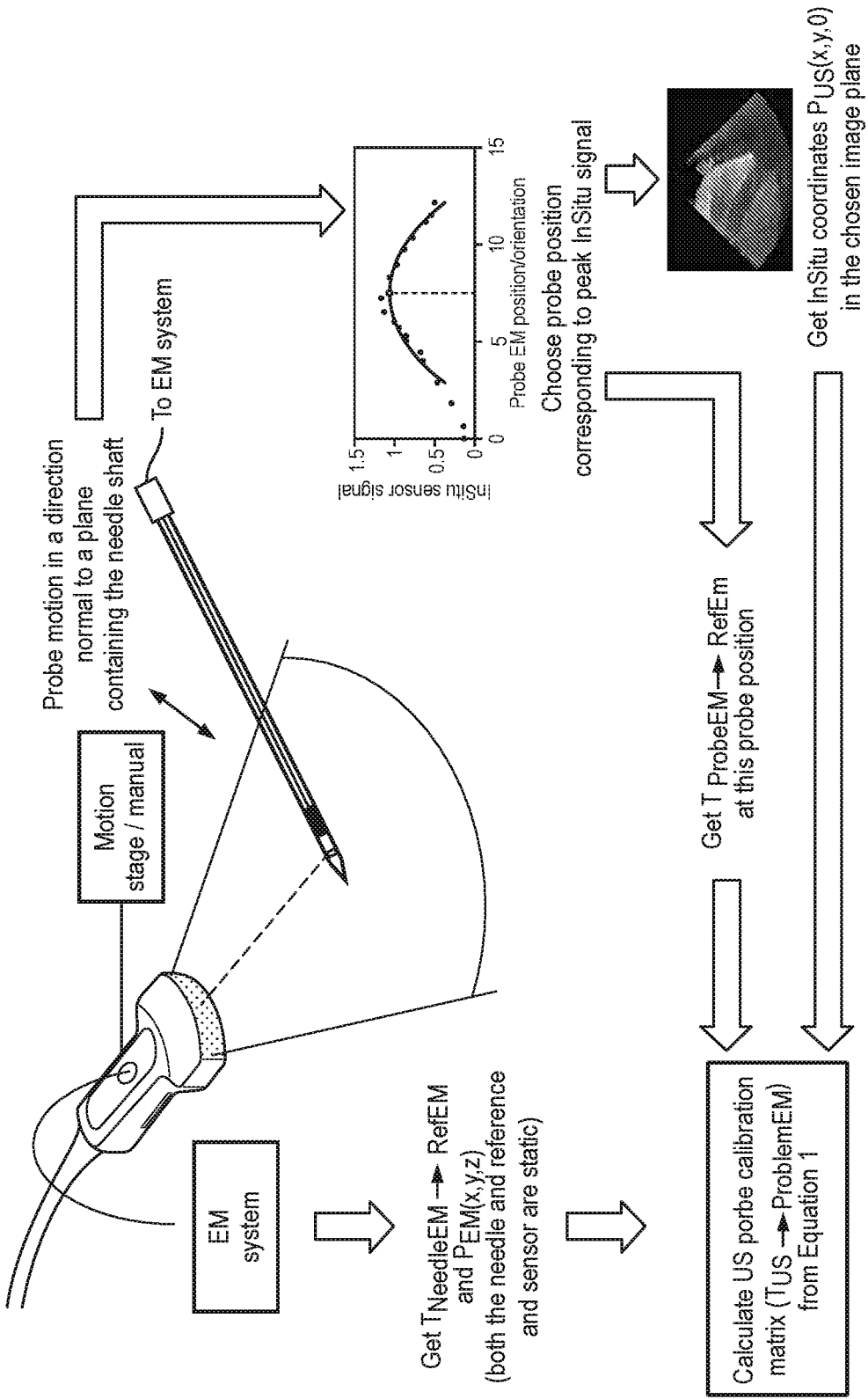
FIG. 9 diagrammatically illustrates a calibration process of the apparatus of FIG. 1 in which the probe is moved relative to the needle.

As shown in FIG. 7, optimization of the position of the calibration needle 16 includes a step 102 of determining candidate locations of the calibration needle 16 using the ultrasound probe 12 with a plurality of different relative positions of the ultrasound probe and the calibration needle (126); for each candidate location, determining a corresponding ultrasound-induced signal strength associated with the determination of the candidate location (128); determining the location of the calibration needle 16 in the ultrasound imaging space as the candidate location having the highest corresponding signal strength (130); and determining the measurement time as a time stamp of the candidate location having the highest corresponding signal strength (132). In some examples, 126 includes operating the robotic apparatus 21 to move the calibration needle 16 relative to the ultrasound probe 12 (or vice versa) to traverse the plurality of different relative positions of the ultrasound probe and the calibration needle. In other examples, the robotic apparatus 21 can include a holder or clamp 23 configured to hold the calibration needle 16 (or alternatively the ultrasound probe 12). In a suitable approach, the calibration needle 16 may be moved over a range of angles θ or linearly by 'x' mm orthogonal to the ultrasound probe 12 sufficient to sweep the tip 32 through the 2D ultrasound plane.

In this embodiment, the calibration workflow can be performed in a water tank or in a tissue-mimicking phantom. The calibration needle 16 and the ultrasound probe 12 should be positioned such that the ultrasound sensors 40 on the calibration needle 16 lie outside an US image plane in an elevational direction (e.g., outside the elevational spread of the US image plane). The calibration needle 16 and the ultrasound probe 12 can be held in place using the holder 23, or alternatively can be held manually by the user.

Next, either the calibration needle 16 or the ultrasound probe 12 is moved (with the other being stationary), such that the ultrasound sensors 40 on the calibration needle 16 first enter the elevational coverage of the US image plane and then eventually exit the image plane. In one example, motion of the calibration needle 16 (shown in FIG. 8) or the ultrasound probe 12 (shown in FIG. 9) can be accomplished using a simple 1D motion stage that is positioned appropriately. In another example, this motion can be performed manually, with the user holding the device to be moved. Rather than a 1D motion the calibration needle 16 can be rotated over a range of angles [θ].

As shown in FIG. 10, for example, the time synchronization described at 106 can be performed by a suitable synchronization operation, for example by interpolation. In one suitable synchronization approach, both data streams (ultrasound and EM) are acquired and stored in the computer 22. Hence, a clock of the computer 22 can be used to regulate/interpret the data. Persistence or interpolation is used to "fill in" missing data from the data stream acquired at a lower acquisition rate and is then temporally matched to the data stream captured at a higher frame rate.

With brief reference to FIG. 10, an illustrative interpolation approach for performing the synchronization operation is described. FIG. 10 shows time stamps (column labeled "Time"), 2D sensor positions (column labeled "US tracking data"), and EM sensor positions (column labeled "EM tracking data"). To illustrate the interpolation consider that at time instant $T_4$, there are missing entries in both the needle tracking and probe tracking data. The missing data may be interpolated using a weighted average of the data immediately preceding and succeeding the current time point $T_4$. For the needle tracking data, this amounts to interpolating $(X_1,Y_1)$ and $(X_2,Y_2)$, such as: $(a_4X_1+b_4X_2, a_4Y_1+b_4Y_2)$, where possible values for the weights $a_4$ and $b_4$ are: $a_4=(T_6-T_4)/(T_6-T_3)$ and $b_4=(T_4-T_3)/(T_6-T_3)$. Similarly, $c_4=(T_5-T_4)/(T_5-T_3)$ and $d_4=(T_4-T_3)/(T_5-T_3)$. Note that this method must be implemented with some time lag, since it utilizes data before and after the missing entry for the interpolation.

With brief reference to FIG. 11, in an alternative embodiment for performing the synchronization operation 134, the latest data can be persisted until the next data point for that stream arrives. This technique can be performed in real-time without any time lag, but may suffer from slightly reduced accuracy as compared with the interpolation approach of FIG. 7.

While the calibration needle 16/ultrasound probe 12 motion is occurring, the following data streams are continuously captured (or intermittently, repeatedly, or otherwise captured): the calibration needle EM sensor 26 position and orientation; the ultrasound probe EM sensor 36 position and orientation; and the ultrasound probe ultrasound sensor 40 information (i.e., signal/SNR, coordinates within US image, frame and line trigger information etc.).

Figure 12:
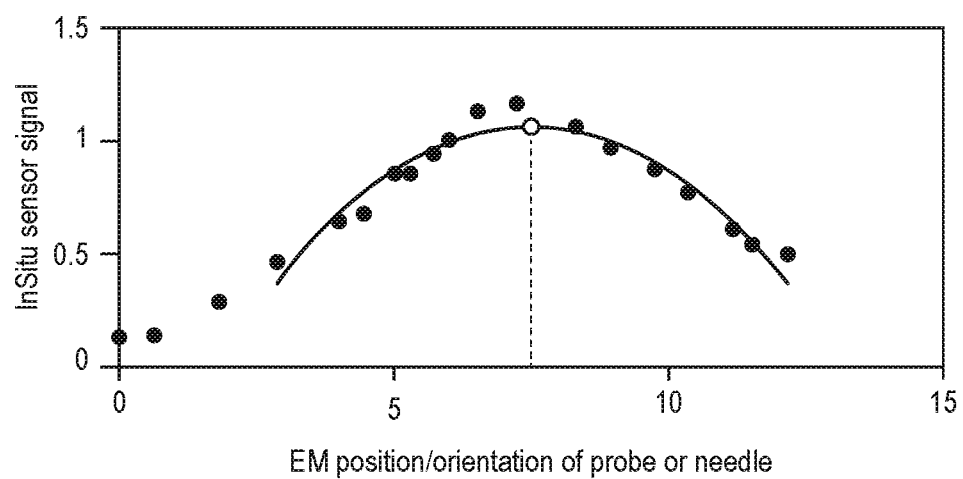
FIG. 12 illustrates a graph of the image frame of the position of a probe or needle of the apparatus of FIG. 1 vs. a magnitude of a sensor signal of the needle.

Referring now to FIG. 12, the US image frame corresponding to the maximum signal/SNR is chosen and the US sensor coordinates in that image frame are recorded. As shown in FIG. 12, a magnitude of the received signal on the ultrasound transducer 28 is analyzed versus the EM readings from the EM sensor 26/36 of the calibration needle 16/ultrasound probe 12 that is translated/rotated. The peak signal strength (or relative signal strength, or any other suitable signal) of the ultrasound transducer 28 is identified and the corresponding image frame and EM readings of the calibration needle 16 and the ultrasound probe 12 are noted.

The corresponding ultrasound probe EM sensor 18 and calibration needle EM sensor 26 coordinates are then chosen, by time-synchronizing the ultrasound data stream with the EM data stream.

The spatial position of the EM sensor 26 on the calibration needle 16 is registered with the spatial position of the ultrasound transducer 28 on the calibration needle 16 using X-ray/fluoroscopy, which can be a one-time process. This transformation is incorporated as part of the $T_{NeedleEM \rightarrow RefEM}$ matrix in Equation 1. The US-EM transformation (i.e., the desired probe calibration, $T_{US \rightarrow ProbeEM}$) can be obtained from the linear equation (equation 1) using the above estimated quantities.

It will be appreciated that the measurement time described above is on the order of milliseconds or less. In one example, the measurement time could be the precise time of sonication of the calibration needle 16. In another example, the measurement time could be some close time such as the start of an ultrasound image.

Example of Use of a Calibrated Probe in an Interventional Procedure

In one example, the interventional procedure is a tracked biopsy procedure, where the anatomical target is defined on a pre-procedural MR image dataset, while the actual intervention (biopsy) is done under 2D US. The below equations describe how the EM, US and MR data streams are all registered together:

$$T_{NeedleEM \rightarrow RefEM} \times p_{NeedleEM}(x,y,z) \text{ [for live needle stream]} \quad \text{(eqn. 2)}$$

$$T_{ProbeEM \rightarrow RefEM} \times T_{US \rightarrow ProbeEM} \times p_{US}(x,y,0) \text{ [for live 2D US stream]} \quad \text{(eqn. 3)}$$

At the beginning of each procedure, the ultrasound probe 12 is "swept" or "rotated" over a series of angles [θ] to acquire multiple 2D images and form a 3D US dataset of the anatomical region of interest. Since each 2D US image in this 3D dataset is indexed to the reference EM sensor 24 of the tracking device 14 (equation 3), the 3D US dataset is obtained directly in the 'RefEM' frame of reference:

Therefore, $p_{3DUS} = p_{RefEM}$ (i.e., a point in the 3D US dataset is already in 'RefEM' space)

$$T_{MR \rightarrow 3DUS} \times p_{MR}(x,y,z) \text{ [for 3D MR dataset]} \quad \text{(eqn. 4)}$$

$T_{MR \rightarrow 3DUS}$ is obtained using image-based registration methods, using, for example, features identifiable in both MR and US. In this manner, the US probe calibration ($T_{US \rightarrow ProbeEM}$) is used to transform the US and MR image data streams into the EM coordinate space.

It will be appreciated that the illustrative computational, data processing or data interfacing components of the apparatus 10 may be embodied as a non-transitory storage medium storing instructions executable by an electronic processor (e.g., the processor 50) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. An apparatus for calibrating electromagnetic (EM) tracking of an associated ultrasound probe, the apparatus comprising:
an EM tracking device including a field generator configured to generate an EM field in an EM-encoded space;
a first EM sensor disposed on the ultrasound probe;
a calibration needle;
a second EM sensor disposed on the calibration needle;
one of (i) at least one ultrasound transducer or (ii) a passive ultrasound reflector disposed on the calibration needle;
at least one processor configured to:
detect a signal based on a response from one of the at least one ultrasound transducer or the passive ultrasound reflector in response to being sonicated by an ultrasound beam emitted by the ultrasound probe;
determine a location of the calibration needle in an ultrasound imaging space at a measurement time using the ultrasound probe from a direction of the ultrasound beam and comparison of the measurement time with a trigger time of the ultrasound beam;
determine an EM-tracked location of the calibration needle at the measurement time from EM tracking by the EM tracking device of the second EM sensor disposed on the calibration needle; and
generate a registration relating the location of the calibration needle in the ultrasound imaging space at the measurement time and the EM-tracked location of the calibration needle at the measurement time.

2. The apparatus according to claim 1, wherein the processor is configured to determine, with the generated registration, a location of at least one ultrasound image in a common coordinate system within the ultrasound imaging space.

3. The apparatus according to claim 1, wherein:
at least one ultrasound transducer is disposed on the calibration needle; and
determining the location of the calibration needle in the ultrasound imaging space at the measurement time using the ultrasound probe includes:
performing an ultrasonic sweep using the ultrasound probe;
detecting a signal emitted by the ultrasound transducer in response to being sonicated by the ultrasound beam emitted by the ultrasound probe wherein the measurement time is a time stamp of the detected signal; and determining the location of the calibration needle in the ultrasound imaging space from a direction of the ultrasound beam and comparison of the measurement time with the trigger time of the ultrasound beam.

4. The apparatus according to claim 1, wherein: a passive ultrasound reflector is disposed on the calibration needle; and
determining the location of the calibration needle in the ultrasound imaging space at the measurement time using the ultrasound probe includes:
performing an ultrasonic sweep using the ultrasound probe;
detecting an ultrasonic reflection from the passive ultrasound reflector disposed on the calibration needle in response to the ultrasonic sweep wherein the measurement time is a time stamp of the detected ultrasonic reflection; and
determining the location of the calibration needle in the ultrasound imaging space from a direction of the ultrasound beam of the ultrasonic sweep that produced the ultrasonic transmission and comparison of the measurement time with a trigger time of the ultrasound beam of the ultrasonic sweep that produced the ultrasonic transmission.

5. The apparatus according to claim 1, wherein determining the location of the calibration needle in the ultrasound imaging space at the measurement time using the ultrasound probe includes:
determining candidate locations of the calibration needle using the ultrasound probe with a plurality of different relative positions of the ultrasound probe and the calibration needle and, for each candidate location, determining a corresponding ultrasound-induced signal strength associated with the determination of the candidate location;
determining the location of the calibration needle in the ultrasound imaging space as the candidate location having the highest corresponding signal strength; and
determining the measurement time as a time stamp of the candidate location having the highest corresponding signal strength.

6. The apparatus according to claim 5, further comprising:
a robotic apparatus configured to move at least one of the calibration needle and the ultrasound probe relative to the other of the calibration needle and the ultrasound probe;
wherein determining the candidate locations includes operating the robotic apparatus to move the calibration needle relative to the ultrasound probe to traverse the plurality of different relative positions of the ultrasound probe and the calibration needle.

7. An apparatus for calibrating tracking of an associated ultrasound probe, the apparatus comprising:
a tracking device configured to locate tracking sensors in a tracking space;
an ultrasound probe tracking sensor disposed on the ultrasound probe;
a calibration needle;
a calibration needle tracking sensor disposed on a calibration needle;
an ultrasound transducer disposed on the calibration needle;
at least one processor configured to:
perform an ultrasound sweep comprising a plurality of ultrasound beams emitted in different directions by the ultrasound probe;
detect a transducer signal generated by the ultrasound transducer in response to sonication of the ultrasound transducer during the ultrasound sweep;
determine a measurement time as a time stamp of the detected transducer signal;
determine a location of the calibration needle in an ultrasound imaging space at the measurement time from a direction of the ultrasound beam that sonicated the ultrasound transducer and comparison of the measurement time with a trigger time of the ultrasound beam that sonicated the ultrasound transducer and the time-of-flight along the ultrasound beam;
determine a tracked location of the calibration needle at the measurement time from tracking by the tracking device of the calibration needle tracking sensor disposed on the calibration needle; and
generate a registration relating the location of the calibration needle in the ultrasound imaging space at the measurement time and the tracked location of the calibration needle at the measurement time.

8. The apparatus according to claim 7, wherein the tracking calibration method further includes:
determining, with the generated registration, a location of at least one ultrasound image in a common coordinate system within the ultrasound imaging space.

9. The apparatus according to claim 7, further comprising:
at least one ultrasound transducer disposed on the calibration needle;
wherein determining the location of the calibration needle in the ultrasound imaging space at the measurement time using the ultrasound probe includes:
performing an ultrasonic sweep using the ultrasound probe;
detecting a signal emitted by the ultrasound transducer in response to being sonicated by an ultrasound beam emitted by the ultrasound probe wherein the measurement time is a time stamp of the detected signal; and
determining the location of the calibration needle in the ultrasound imaging space from a direction of the ultrasound beam and comparison of the measurement time with a trigger time of the ultrasound beam.

10. The apparatus according to claim 7, wherein determining the location of the calibration needle in the ultrasound imaging space at the measurement time using the ultrasound probe includes:
acquiring an ultrasound image in the ultrasound imaging space; and
determining the location of the calibration needle in the ultrasound imaging space by detecting an image of the calibration needle in the ultrasound image, wherein the measurement time is an acquisition time stamp of the image of the calibration needle in the ultrasound image.

11. The apparatus according to claim 7, wherein determining the location of the calibration needle in the ultrasound imaging space at the measurement time using the ultrasound probe includes:
determining candidate locations of the calibration needle using the ultrasound probe with a plurality of different relative positions of the ultrasound probe and the calibration needle and, for each candidate location, determining a corresponding ultrasound-induced signal strength associated with the determination of the candidate location;
determining the location of the calibration needle in the ultrasound imaging space as the candidate location having the highest corresponding signal strength; and determining the measurement time as a time stamp of the candidate location having the highest corresponding signal strength.

12. The apparatus according to claim 11, further comprising:
   a robotic apparatus configured to move at least one of the calibration needle and the ultrasound probe relative to the other of the calibration needle and the ultrasound probe;
   wherein determining the candidate locations includes operating the robotic apparatus to move the calibration needle relative to the ultrasound probe to traverse the plurality of different relative positions of the ultrasound probe and the calibration needle.

\* \* \* \* \*